United States Patent
Shibata et al.

(10) Patent No.: US 10,765,451 B2
(45) Date of Patent: Sep. 8, 2020

(54) RETRACTOR FOR SMALL-INCISION ENDOSCOPIC SURGERY

(71) Applicants: OSAKA CITY UNIVERSITY, Osaka-shi (JP); OZK CO., LTD., Yao-shi (JP); SHINWA SYOJI CO., LTD., Higashiosaka-shi (JP)

(72) Inventors: Toshihiko Shibata, Osaka (JP); Haruhiko Yamasaki, Yao (JP); Katsunori Mitsuhashi, Yao (JP); Yoshiro Morishita, Higashiosaka (JP)

(73) Assignees: OSAKA CITY UNIVERSITY, Osaka-shi (JP); OZK CO., LTD., Yao-shi (JP); SHINWA SYOJI CO., LTD., Higashiosaka-shi (JP)

( * ) Notice: Subject to any disclaimer, the term of this patent is extended or adjusted under 35 U.S.C. 154(b) by 0 days.

(21) Appl. No.: 16/319,908

(22) PCT Filed: Jul. 21, 2017

(86) PCT No.: PCT/JP2017/026429
§ 371 (c)(1),
(2) Date: Jan. 23, 2019

(87) PCT Pub. No.: WO2018/021174
PCT Pub. Date: Feb. 1, 2018

(65) Prior Publication Data
US 2019/0269393 A1    Sep. 5, 2019

(30) Foreign Application Priority Data
Jul. 25, 2016   (JP) ................. 2016-145697

(51) Int. Cl.
*A61B 17/34*   (2006.01)
*A61B 17/02*   (2006.01)
*A61M 29/00*   (2006.01)

(52) U.S. Cl.
CPC .......... *A61B 17/3431* (2013.01); *A61B 17/02* (2013.01); *A61B 17/0218* (2013.01);
(Continued)

(58) Field of Classification Search
CPC ................ A61B 17/02; A61B 17/0218; A61B 2017/0225; A61B 17/3417;
(Continued)

(56) References Cited

U.S. PATENT DOCUMENTS

| 4,610,243 A | 9/1986 | Ray |
| 6,162,172 A | 12/2000 | Cosgrove |

(Continued)

FOREIGN PATENT DOCUMENTS

| DE | 202016101334 U1 * | 5/2016 | ............. A61B 17/02 |
| JP | 61-268241 A | 11/1986 | |

(Continued)

OTHER PUBLICATIONS

International Search Report for International Application No. PCT/JP2017/026429 dated Oct. 3, 2017 (2 Sheets).

*Primary Examiner* — Larry E Waggle, Jr.
(74) *Attorney, Agent, or Firm* — Kratz, Quintos & Hanson, LLP

(57) ABSTRACT

A retractor holds a surgical incision in a body in an opened state to ensure a surgical field in small-incision endoscopic surgery, and includes a base body that is a thin plate made of tin having a purity of not less than 99.9% and has an elongated rectangular shape in an extended state of the base body. The retractor, in an extended form in a rectangular shape or in a rounded form in a small shape, can be inserted from a small incision wound into the body, and can easily be delivered to the surgical incision in the body by a surgical instrument. The base body is bent and deformed into a desired shape by the surgical instrument and is applied to the (Continued)

surgical incision in the body, so that the surgical incision can be held in an opened state so as to ensure the surgical field.

11 Claims, 9 Drawing Sheets

(52) U.S. Cl.
CPC ......... *A61B 17/3417* (2013.01); *A61M 29/00* (2013.01); *A61B 17/3439* (2013.01); *A61B 2017/0225* (2013.01); *A61B 2017/348* (2013.01)

(58) Field of Classification Search
CPC ............ A61B 17/3431; A61B 17/3439; A61B 17/348; A61B 2017/3492; A61M 29/00
See application file for complete search history.

(56) References Cited

U.S. PATENT DOCUMENTS

| | | | | |
|---|---|---|---|---|
| 6,733,443 B2* | 5/2004 | Rupp | ..................... | A61B 17/02 600/210 |
| 7,338,441 B2* | 3/2008 | Houser | .............. | A61B 17/0218 600/206 |
| 7,699,864 B2* | 4/2010 | Kick | ................... | A61B 17/3439 600/184 |
| 2002/0116025 A1* | 8/2002 | Haab | ....................... | A61B 17/02 606/206 |
| 2007/0038032 A1 | 2/2007 | De Canniere | | |
| 2009/0216089 A1 | 8/2009 | Davidson | | |

FOREIGN PATENT DOCUMENTS

| | | | | |
|---|---|---|---|---|
| JP | 2006-016681 A | | 1/2006 | |
| JP | 2006-304819 A | | 11/2006 | |
| JP | 2007-082674 A | | 4/2007 | |
| JP | 2007-144138 A | | 6/2007 | |
| JP | 2009-504214 A | | 2/2009 | |
| JP | 2013-090856 A | | 5/2013 | |
| JP | 2013090856 A | * | 5/2013 | |
| JP | 2016-083101 A | | 5/2016 | |
| WO | WO-2007004531 A1 | * | 1/2007 | ......... A61B 17/3421 |
| WO | WO-2015178311 A1 | * | 11/2015 | ............. A61B 17/02 |

* cited by examiner

RETRACTOR FOR SMALL-INCISION ENDOSCOPIC SURGERY

TECHNICAL FIELD

The present invention relates to a retractor which, in small-incision endoscopic surgery, is inserted from a small incision wound made in the chest or the abdomen, and holds a surgical incision made in the body during the surgery in an opened state, to ensure a surgical field.

BACKGROUND ART

In small-incision endoscopic surgery, small incision wounds are made at several places in the chest or the abdomen, and the surgery is performed using a surgical instrument such as forceps or an electric knife while the inside of a body cavity is viewed with a thoracoscope or a laparoscope. Accordingly, compared with thoracotomy/laparotomy in which a large incision is made, postoperative pain is very little and also the scar is substantially inconspicuous. Therefore, invasiveness of the surgical treatment can be significantly reduced, and at the same time, the quality of life (QOL) can be greatly improved.

In such small-incision endoscopic surgery, the surgical field is often ensured by: a surgical instrument having a hook-shaped leading end being inserted from the small incision wound; and a surgical assistant pulling, by hand, the leading end of the surgical instrument hooked on a surgical incision in the body (hereinafter, this operation will be referred to as "incision using a traction hook").

In addition to the incision using a traction hook, retractors using elastic plate-shaped bodies are used for ensuring the surgical field. Here, those retractors are not for use in small-incision endoscopic surgery (see FIG. 1 to FIG. 5 of Patent Literature 1 and FIG. 4 of Patent Literature 2, for example).

In Patent Literature 1, a retractor is formed into a cylindrical shape with a large outer diameter by being rounded so that the front end and the back end thereof are slidable. The entirety of the retractor is rounded into a small cylinder of a small diameter, and is then inserted into a surgical incision. The retractor expands due to elastic force in the surgical incision, thereby widening the surgical incision.

In Patent Literature 2, a shape memory alloy that has a shape memory property at a living-body temperature (about 37° C.) is formed into a plate shape, and then, the resultant shape memory alloy is caused to memorize a cylindrical shape with a large outer diameter, to obtain a retractor. The entirety of the retractor is rounded into a small cylinder with a small diameter, and is then inserted into a surgical incision. The retractor expands in the surgical incision due to the shape memory effect caused by the body temperature of the patient, thereby widening the surgical incision.

CITATION LIST

Patent Literature

[PTL 1] Japanese Unexamined Patent Application Publication No. 2007-082674
[PTL 2] Japanese Unexamined Patent Application Publication No. 2006-304819

SUMMARY OF THE INVENTION

Problems to be Solved by the Invention

With the incision using a traction hook as described above, and the retractor as in Patent Literature 1 or 2, a surgical field desired by the operator (surgeon) has difficulty in being ensured, and the surgical field cannot be ensured or changed flexibly in accordance with the surgical site and the surgical situation.

In addition, in the incision using a traction hook, the burden on the surgical assistant is large and the surgery cost increases due to the labor cost of the surgical assistant.

If the surgical assistant does not perform the traction, an instrument for holding the traction hook outside the body is required, and thus, the operation in the small incision surgery is hindered.

The retractor as in Patent Literature 1 or 2 may temporarily be used in small-incision endoscopic surgery. In such a case, if the retractor with the plate-shaped body being rounded so as to have a small diameter (see the left drawing in FIG. 1 of Patent Literature 1 and the lower drawing in FIG. 4 of Patent Literature 2, for example) is inserted into the body from the small incision wound and then released from the hand, the retractor expands due to elastic restoring force or the shape memory property. This causes the diameter of the cylinder to be increased (the right drawing in FIG. 1 of Patent Literature 1 and the upper drawing in FIG. 4 of Patent Literature 2, for example). Thus, the work of moving the retractor to the surgical incision in the body to dispose the retractor thereat is difficult.

In addition, even if the surgical incision in the body can be held in an opened state by use of the retractor as in Patent Literature 1 or 2 and the surgical field is successfully ensured, the retractor in the use state thereof is in a cylindrical shape with a large outer diameter. This causes the work of taking the retractor out of the body to be very difficult.

In view of the above-described situation, an object of the present invention is to provide a retractor, for small-incision endoscopic surgery, which can easily ensure a surgical field as desired by an operator, can flexibly ensure and change the surgical field in accordance with the surgical site and the surgical situation, and can be easily moved to a desired position in the surgical site and taken out after the surgery.

Solution to the Problems

In order to solve the above problem, a retractor for small-incision endoscopic surgery according to the present invention is a retractor holding a surgical incision made in a body during the surgery in an opened state to ensure a surgical field in the small-incision endoscopic surgery, the retractor comprising a base body that is a thin plate made of tin having a purity of not less than 99.9%, and has an elongated rectangular shape in an extended state of the base body, wherein the retractor is inserted from a small incision wound into the body, with the base body being extended into a rectangular shape, or being rounded into a small shape, and the retractor is delivered to the surgical incision in the body by a surgical instrument used in the small-incision endoscopic surgery, and is used in a state that the base body is bent and deformed into a desired form by the surgical instrument and is applied to the surgical incision.

Further, in order to solve the above problem, a retractor for small-incision endoscopic surgery according to the present invention is a retractor holding a surgical incision made in a body during the surgery in an opened state to ensure a surgical field in the small-incision endoscopic surgery, the retractor comprising:

a base body that is a thin plate made of tin having a purity of not less than 99.9%, and has an elongated rectangular shape in an extended state of the base body; and a fixing means configured to fix a leading end portion of a surgical hook to the base body, wherein the retractor is inserted from a small incision wound into the body, with the base body being extended into a rectangular shape, or being rounded into a small shape, in a state that the leading end portion of the surgical hook is fixed to the base body by the fixing means to hold the retractor by the surgical hook, and the retractor is delivered to the surgical incision in the body by the surgical hook, and is used in a state that the base body is bent and deformed into a desired form by a surgical instrument used in the small-incision endoscopic surgery, and is applied to the surgical incision.

Here, preferably, the base body has an external shape with a width of 1 to 5 cm, a length of 3 to 20 cm, and a thickness of 0.5 to 2 mm, when being extended into the rectangular shape.

According to such configurations of the retractor for small-incision endoscopic surgery, the base body of the retractor is a thin plate made of tin having a purity of not less than 99.9% and has an elongated rectangular shape in an extended state of the base body. Therefore, the retractor can be inserted into the body from the small incision wound made in the chest or the abdomen with the base body being extended into a rectangular shape, or being rounded into a small shape, and can be easily delivered by a surgical instrument used in the small-incision endoscopic surgery or a surgical hook fixed to the base body, to the surgical incision made in the body during the surgery.

In addition, since the base body of the retractor is made of tin having a purity of not less than 99.9%, the base body has a high flexibility in particular. Thus, the base body can be easily bent and deformed into a desired form by use of the surgical instrument.

Therefore, the base body is bent and deformed into a desired shape and applied to the surgical incision in the body, thereby holding the surgical incision in an opened state so as to ensure the surgical field.

In order to hold the surgical incision in an opened state, the width of the base body of the retractor is selected in a range of 1 to 5 cm and the length of the base body is selected in a range of 3 to 20 cm in accordance with the size required for a use place, under a state that the base body is extended into a rectangular shape. Then, in order to ensure the flexural rigidity necessary for the use place, the thickness of the base body is selected in a range of 0.5 to 2 mm Furthermore, since the base body of the retractor can be easily deformed, a surgical field as desired by an operator (surgeon) can be easily ensured, and the surgical field can be ensured and changed flexibly in accordance with the surgical site and the surgical situation.

In addition, the operator operates the retractor, thereby eliminating the burden on the surgical assistant, such as the incision using a traction hook, and reducing the surgery cost due to reduction of the labor cost.

Furthermore, the base body of the retractor is made of tin having a purity of not less than 99.9%. Accordingly, after the base body is bent and deformed into a desired form and used, the base body can be easily restored by use of the surgical instrument into a form of being extended into a rectangular shape or a form of being rounded into a small shape. Therefore, the retractor can easily be taken out of the body through the small incision wound.

In particular, the retractor includes the fixing means and the leading end portion of the surgical hook is fixed to the base body of the retractor. Accordingly, the retractor can easily and assuredly be delivered to the surgical incision made in the body during the surgery, in a state that the leading end portion of the surgical hook is fixed to the base body to hold the retractor by the surgical hook. After the surgery, the retractor can easily and assuredly be taken out of the body through the small incision wound. Furthermore, the base body of the retractor is fixed to the leading end portion of the surgical hook, thereby assuredly preventing the retractor from being lost in the body.

Further preferably, a bent portion bent in a loop shape about an axis parallel to a short direction of the base body is provided in an end portion in a longitudinal direction of the base body, in a state that the base body is extended into the rectangular shape.

Further, a tubular body having a through-hole parallel to a short direction of the base body may be provided in an end portion in a longitudinal direction of the base body, in a state that the base body is extended into the rectangular shape.

According to such configurations of the retractor for small-incision endoscopic surgery, the work of deforming the base body of the retractor into a desired shape can easily be performed by operating the surgical instrument used in the small-incision endoscopic surgery, with the bent portion or an appropriate place of the tubular body being gripped by an end effector such as a jaw of the surgical instrument.

Further preferably, the base body has, on one or both surfaces thereof, an anti-slip protrusion.

According to such a configuration of the retractor for small-incision endoscopic surgery, the retractor is less likely to be displaced from the surgical incision in the body by the anti-slip protrusion on the surface of the base body of the retractor. This eliminates hindrance of the surgery due to unexpected displacement of the surgical incision, and damaging a non-affected area due to unexpected contact thereto of the surgical instrument or the like. In addition, the surgery can be efficiently performed in a state that the surgical field is assuredly maintained.

Further preferably, the base body is deformed into a cylindrical shape, and has protrusions arranged in a helical manner on a cylindrical face of the cylindrical shape.

According to such a configuration of the retractor for small-incision endoscopic surgery, the base body of the retractor may be deformed into a cylindrical shape and used. In such a case, if the protrusions arranged in the helical manner on the cylindrical face are arranged in a right-hand thread manner, the retractor advances when rotated clockwise, and the retractor retreats when rotated counterclockwise. If the protrusions arranged in the helical manner on the cylindrical face are arranged in a left-hand thread manner, the retractor advances when rotated counterclockwise and the retractor retreats when rotated clockwise.

Therefore, operation of moving the retractor in an advancing direction or a retreating direction with respect to the surgical incision in the body is facilitated.

In addition, due to the protrusions arranged in the helical manner on the cylindrical face, the retractor is less likely to be displaced from the surgical incision. This eliminates hindrance of the surgery due to unexpected displacement of the surgical incision, and damaging a non-affected area due to unexpected contact thereto of the surgical instrument or the like. In addition, the surgery can be efficiently performed in a state that the surgical field is assuredly maintained.

Further preferably, a through-hole in a thickness direction of the base body is provided in an end portion in a longitudinal direction of the base body, in a state that the base body is extended into the rectangular shape.

According to such a configuration of the retractor for small-incision endoscopic surgery, a thread is passed through a through-hole provided in the end portion in the longitudinal direction of the base body and one end of the thread is fixed, and then the other end of the thread is drawn out to the outside of the body through the small incision wound with the retractor remaining in the body, thereby assuredly preventing the retractor from being lost in the body.

In addition, if the base body is easily displaced from the surgical incision in the body, it is also possible to fix the base body by fixing the base body to a nearby tissue by means of the thread passed through the through-hole.

Advantageous Effects of the Invention

As described above, the retractor for small-incision endoscopic surgery according to the present invention exhibits outstanding effects as mainly indicated in (1) to (5) below.
(1) The retractor can be inserted into the body from a small incision wound made in the chest or the abdomen in a form in which the base body is extended into a rectangular shape or is rounded into a small shape, and can easily be delivered by the surgical instrument used in the small-incision endoscopic surgery or the surgical hook fixed to the base body, to the surgical incision made in the body during the surgery.
(2) The base body is bent and deformed into a desired shape, and is applied to the surgical incision in the body, thereby holding the surgical incision in an opened state so as to ensure the surgical field.
(3) A surgical field as desired by an operator (surgeon) can easily be ensured, and the surgical field can be ensured and changed flexibly in accordance with the surgical site and the surgical situation.
(4) The operator operates the retractor, thereby eliminating the burden on the surgical assistant as in the case of the incision using a traction hook, and the surgery cost can be reduced due to reduction of the labor cost.
(5) After use, the base body can be restored into a form in which the base body is extended into a rectangular shape or is rounded into a small shape, and then the retractor can easily be taken out of the body through the small incision wound.

DESCRIPTION OF EMBODIMENTS

Next, an embodiment of the present invention will be described in detail with reference to the accompanying drawings. The present invention is not limited to the embodiment shown in the accompanying drawings and includes all embodiments that meet the requirements described in the claims.

Figure 1:
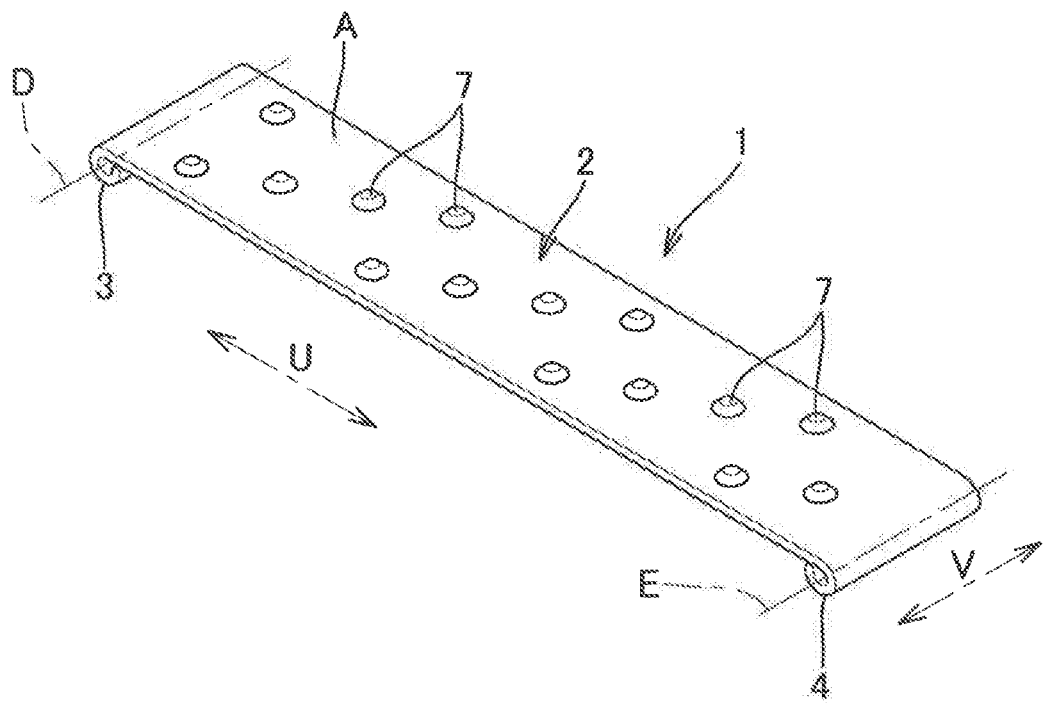
FIG. 1 is a perspective view showing a form in which a retractor for small-incision endoscopic surgery according to an embodiment of the present invention is extended into a rectangular shape.

A retractor 1 for small-incision endoscopic surgery according to an embodiment of the present invention holds a surgical incision made in a body during small-incision endoscopic surgery, in an opened state, to ensure a surgical field. An extended form of the retractor 1 into a rectangular shape is shown in a perspective view in FIG. 1, a front view in FIG. 2A, and a bottom view in FIG. 2B.

The retractor 1 includes a base body 2 that is a thin plate made of tin having a purity of not less than 99.9%, and has an elongated rectangular shape in its extended state. The retractor 1 also includes bent portions 3 and 4 respectively bent in loop shapes about axes D, E parallel to a short direction V, at end portions in a longitudinal direction U of the base body 2 in its extended form into a rectangular shape. In addition, the retractor 1 further includes protrusions 7, 7, . . . on a surface A of the base body 2.

Tin has a tetragonal β tin (beta-tin) structure as a crystal structure at normal temperature/normal pressure, is a soft and silvery-white metal, is not affected by oxygen due to an oxide film, and does not react with water.

Such tin is used as the material of the base body 2, and thus the purity of tin forming the base body 2 is not less than 99.9%. That is, the base body 2 contains tin by not less than 99.9% by weight. Thus, the base body 2 has a high flexibility in particular, and can be easily bent by hand or a surgical instrument, for example.

The external shape of the base body 2 in the extended form into a rectangular shape has a width W of 1 to 5 cm, a length L of 3 to 20 cm, and a thickness T of 0.5 to 2 mm. In order to hold a surgical incision in the body in an opened state, the width W of the base body 2 is selected in a range of 1 to 5 cm and the length L of the base body 2 is selected in a range of 3 to 20 cm depending on the size required for a use place. Then, in order to ensure the flexural rigidity necessary for the use place, the thickness T of the base body 2 is selected in a range of 0.5 to 2 mm As for the base body 2, a 3N tin ingot (purity: not less than 99.9%), a 4N tin ingot (purity: not less than 99.99%), or such a tin ingot having a high purity and a very large ductility is used. The ductility indicates the limit to which the material flexibly deforms without being broken. The tin ingot is processed into a plate shape having a desired thickness not through casting but through forging or rolling, and then, the plate-shaped tin ingot is cut into a rectangular shape having a desired width and a desired length, whereby the base body 2 is shaped. Being shaped in this manner, the base body 2 has the same purity as the tin ingot, and thus has a purity of not less than 99.9%.

In addition, through press working, the protrusions 7, 7, . . . are formed on the surface A of the base body 2, and the bent portions 3, 4 are formed in the end portions in the longitudinal direction U of the base body 2.

Figure 2A:
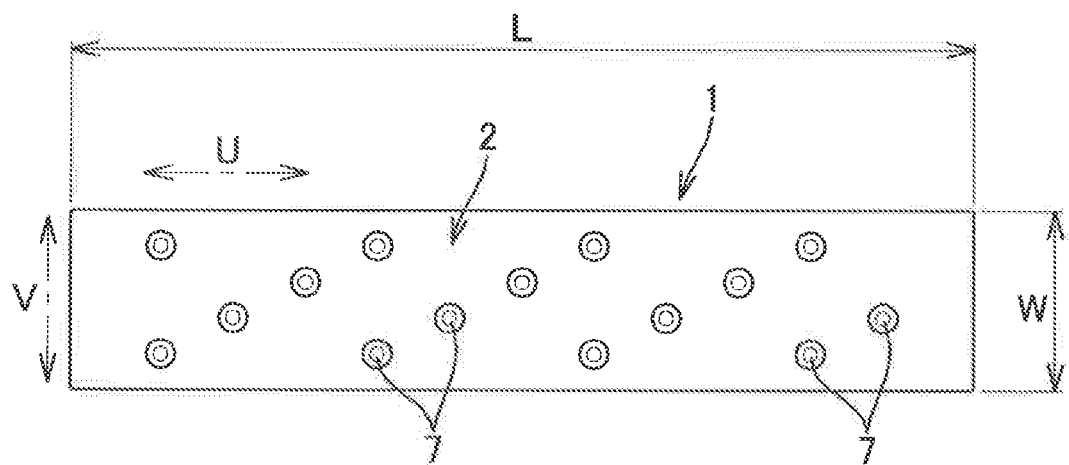
FIG. 2A is a front view of the form of the retractor shown in FIG. 1.
Figure 2B:
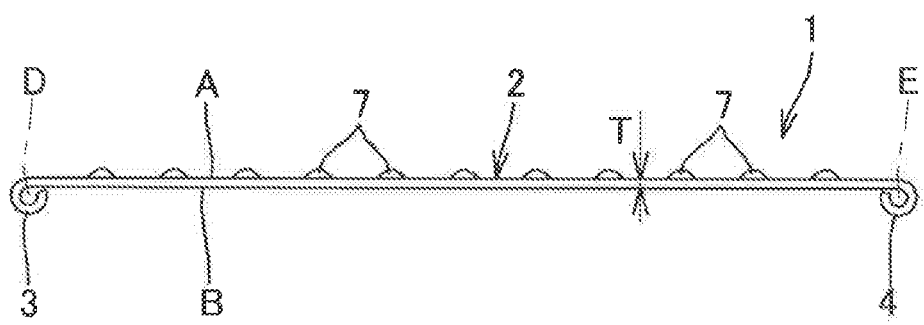
FIG. 2B is a bottom view of the form of the retractor shown in FIG. 1.
Figure 3A:
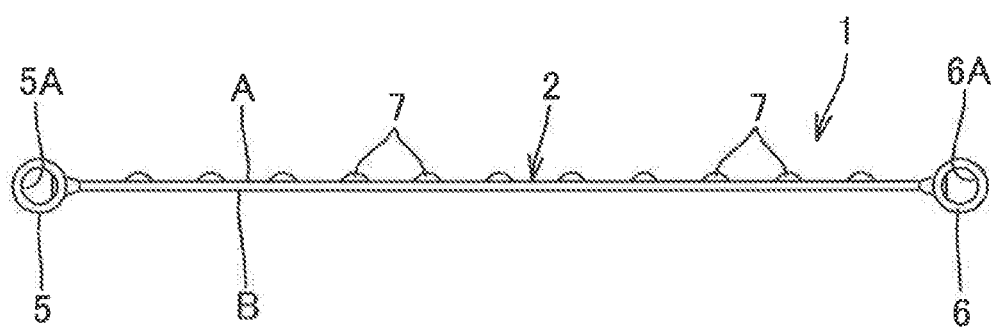
FIG. 3A is a bottom view showing a modification in which bent portions in end portions in the longitudinal direction of a base body are replaced with tubular bodies which are separate bodies from the base body.
Figure 3B:
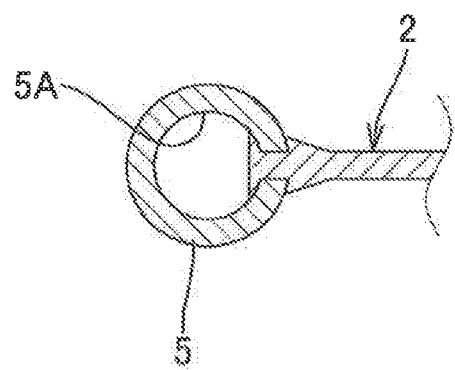
FIG. 3B is an enlarged longitudinal cross-sectional bottom view of a main part of the modification shown in FIG. 3A.

As shown in a bottom view in FIG. 3A and an enlarged longitudinal cross-sectional bottom view of a main part shown in FIG. 3B, the base body 2 may have, in the end portions in the longitudinal direction thereof, tubular bodies 5, 6 respectively having through-holes 5A, 6A parallel to the short direction of the base body 2, instead of the bent portions 3, 4 that are shown in the bottom view in FIG. 2B, in a state that the base body 2 is extended into a rectangular shape.

The tubular bodies 5, 6 are separate bodies from the base body 2, and are made of synthetic resin such as polyamide (PA) resin, polyethylene terephthalate (PET) resin, or polyether ether ketone (PEEK) resin, for example.

In the retractor 1 for small-incision endoscopic surgery as described above, the base body 2 is a thin plate made of tin having a purity of not less than 99.9% and has an elongated rectangular shape in an extended state of the base body 2. Therefore, the retractor 1 can be inserted into the body from a small incision wound made in the chest or the abdomen with the base body 2 being extended into a rectangular shape, or being rounded into a small shape, and can easily be delivered by a surgical instrument used in the small-incision endoscopic surgery, to a surgical incision made in the body during the surgery.

In addition, the base body 2 is made of tin having a purity of not less than 99.9%. Thus, the base body 2 can easily be bent and deformed into a desired form by use of the surgical instrument. For example, the base body 2 can easily be shaped into a cylindrical shape as shown in a perspective view in FIG. 4.

The base body 2 can easily be deformed into a desired shape by gripping an appropriate place of the bent portion 3, 4 with an end effector such as a jaw of the surgical instrument, and performing operation with the surgical instrument.

In a configuration in which not the bent portions 3, 4 but the tubular bodies 5, 6 are provided as in FIG. 3A, such operation can be performed by gripping an appropriate place of the tubular body 5, 6 with an end effector of the surgical instrument, and performing operation with the surgical instrument.

Figure 4:
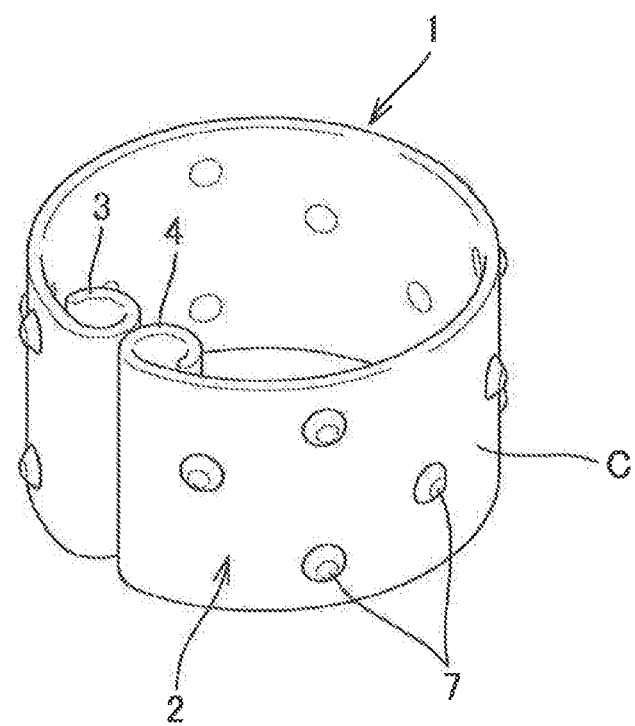
FIG. 4 is a perspective view showing a form in which the base body is deformed into a cylindrical shape as one example of a desired shape of the retractor.

The base body 2 of the retractor 1 is bent and deformed into a desired shape as shown in FIG. 4, and applied to the surgical incision in the body, thereby holding the surgical incision in an opened state, so as to ensure the surgical field.

In addition, the base body 2 of the retractor 1 can easily be deformed, and thus a surgical field as desired by an operator (surgeon) can easily be ensured. The surgical field can also be ensured and changed flexibly in accordance with the surgical site and the surgical situation.

Further, the operator operates the retractor 1, thereby eliminating the burden on the surgical assistant, such as the incision using a traction hook, and reducing the surgery cost due to reduction of the labor cost.

Furthermore, the base body 2 of the retractor 1 is made of tin having a purity of not less than 99.9%, thereby easily restoring a form of the base body 2 into an extended rectangular shape or a rounded small shape by use of the surgical instrument, after the base body 2 is bent and deformed into a desired form and used. Therefore, the retractor 1 can easily be taken out of the body through the small incision wound.

In the use state as shown in FIG. 4, the protrusions 7, 7, . . . are present on a cylindrical face C that is the face opposed to the surgical incision in the retractor 1, and the protrusions 7, 7, . . . function as anti-slip protrusions. That is, due to the anti-slip protrusion, the retractor 1 is less likely to be displaced from the surgical incision in the body. This eliminates hindrance of the surgery due to unexpected displacement of the surgical incision, and damaging a non-affected area due to unexpected contact thereto of the surgical instrument or the like. In addition, the surgery can be efficiently performed in a state that the surgical field is assuredly maintained.

Figure 5A:
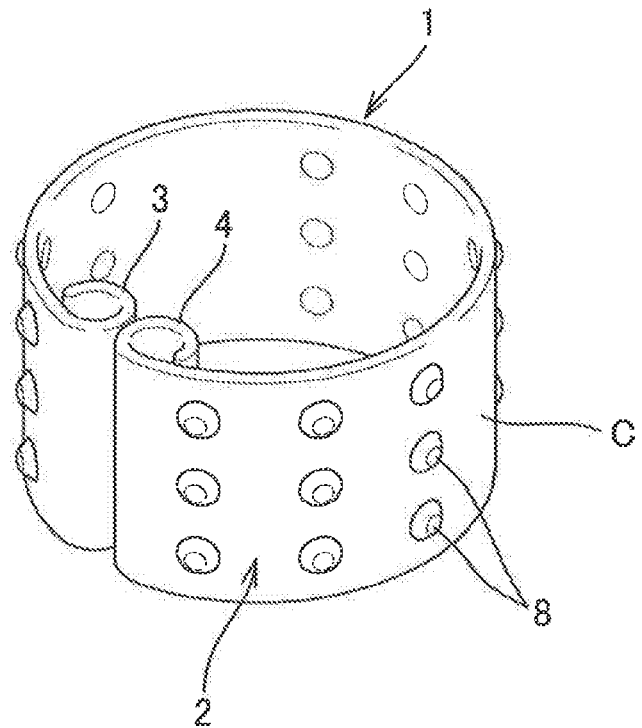
FIG. 5A is a perspective view showing a modification of protrusions formed on a cylindrical face, and shows an example in which the protrusions are provided in three rows in the width direction.
Figure 5B:
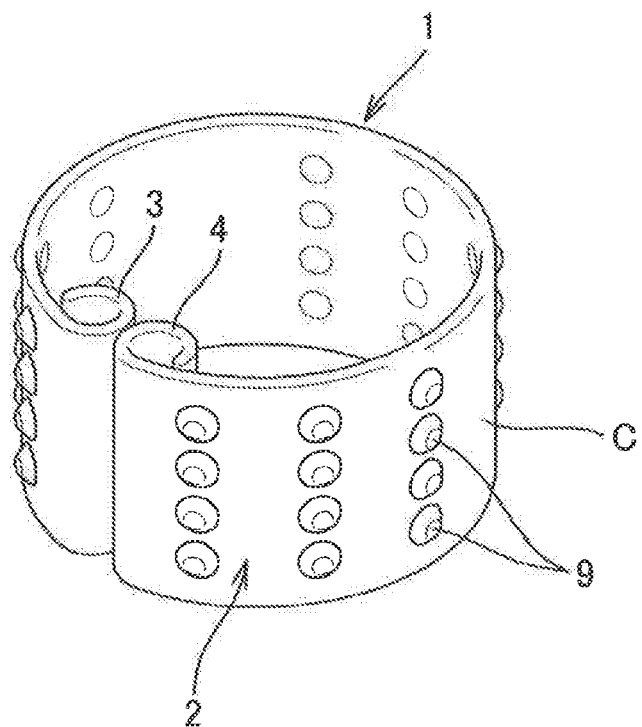
FIG. 5B is a perspective view showing a modification of the protrusions formed on the cylindrical face, and shows an example in which the protrusions are provided in four rows in the width direction.

The anti-slip protrusions may be protrusions 8, 8, . . . provided in three rows in the width direction as shown in a perspective view in FIG. 5A, or may be protrusions 9, 9, . . . as shown in a perspective view in FIG. 5B, and are not limited to the form of the present embodiment.

Figure 6:
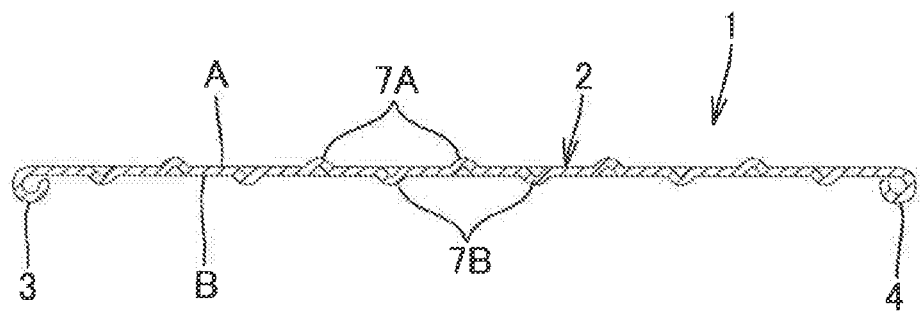
FIG. 6 is a longitudinal cross-sectional bottom view showing an example in which the protrusions are formed on both surfaces of the base body.

In addition, as shown in a longitudinal cross-sectional bottom view in FIG. 6, protrusions 7A, 7A, . . . and 7B, 7B, . . . may be provided on both surfaces A, B of the base body 2. According to this form, each of the surfaces A and B can be used as a face that is opposed to the surgical incision, without distinguishing the surfaces A, B from each other.

Such double-side processing can easily be performed by double-side embossing or the like in which the material is passed between, in pressure contact with, a pair of emboss-ing rolls having recesses and protrusions on the surfaces thereof.

Further, the protrusions 7, 7, . . . shown in the front view in FIG. 2A and the perspective view in FIG. 4 are provided in a helical manner on the cylindrical face C in FIG. 4 obtained by deforming the base body 2 into a cylindrical shape.

If the helically arranged protrusions formed on the cylindrical face C are in a right-hand thread arrangement, the retractor 1 advances when rotated clockwise, and the retractor 1 retreats when rotated counterclockwise. If the helically arranged protrusions formed on the cylindrical face C are in a left-hand thread arrangement, the retractor 1 advances when rotated counterclockwise, and the retractor 1 retreats when rotated clockwise.

Therefore, operation of moving the retractor 1 in an advancing direction or a retreating direction with respect to the surgical incision in the body is facilitated.

The "protrusion" in the present invention may be protrusions (the protrusions are separated from one another) independently protruding from the surface A (the cylindrical face C) and the surface B as in the present embodiment, or may be in a form of a continuous line (protruding ridge) or the like.

Figure 7:
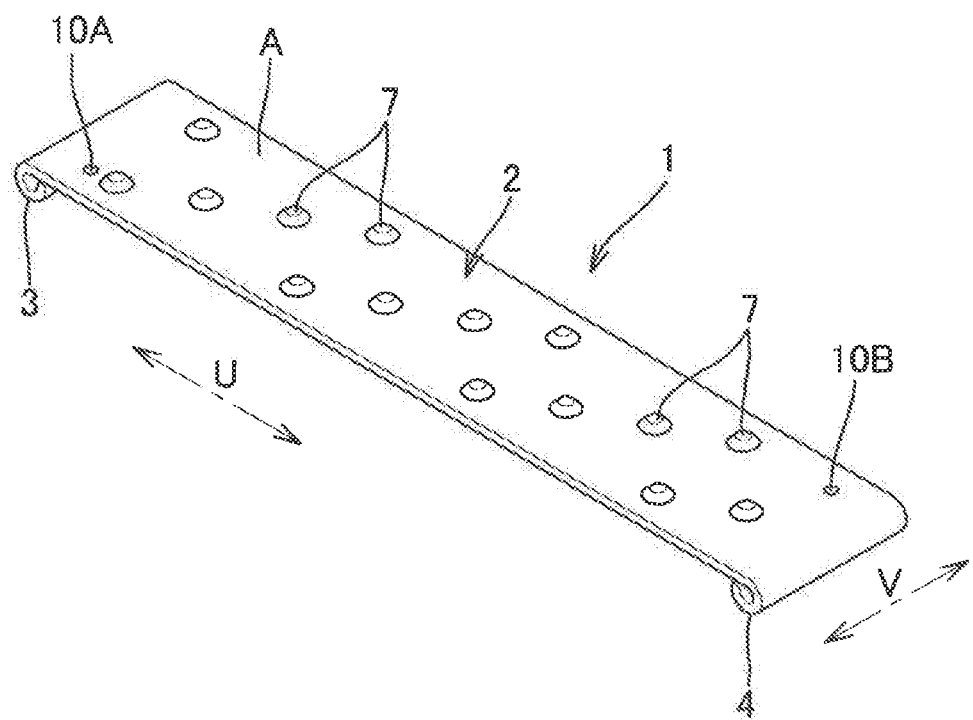
FIG. 7 is a perspective view showing through-holes in the thickness direction provided in end portions in the longitudinal direction of the base body.

The retractor 1 shown in a perspective view in FIG. 7 includes through-holes 10A, 10B in the thickness direction of the base body 2, in end portions in the longitudinal direction U of the base body 2.

Thus, if a thread is passed through the through-hole 10A or 10B provided in the end portion in the longitudinal direction of the base body 2 and one end of the thread is fixed, and then the other end of the thread is drawn out to the outside of the body through the small incision wound in a use state that the retractor 1 is left in the body, it is possible to assuredly prevent the retractor 1 from being lost in the body.

In addition, if the base body 2 is easily displaced from the surgical incision in the body, the base body 2 can also be fixed by being fixed to a nearby tissue by means of the thread passed through the through-hole 10A or 10B.

Figure 8:
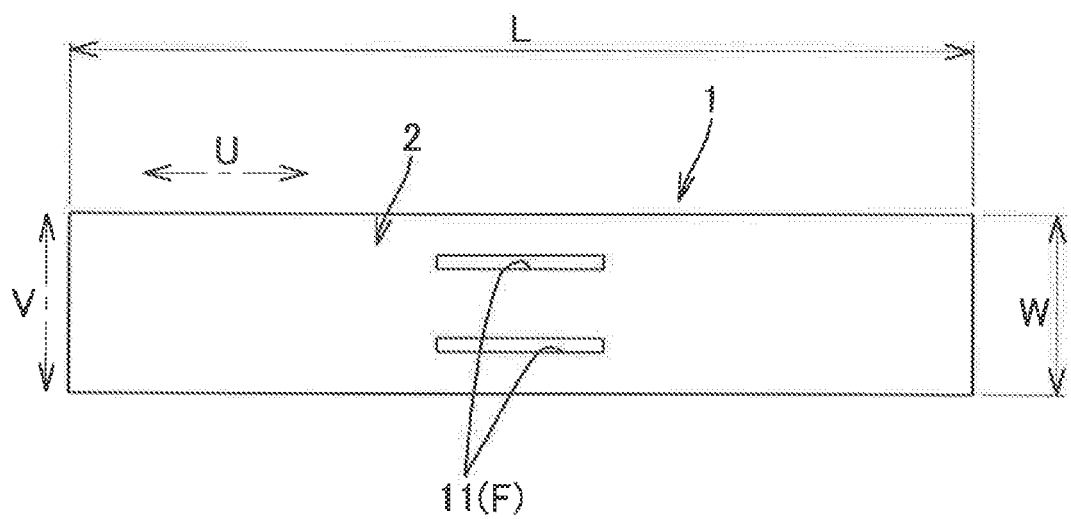
FIG. 8 is a front view of a modification in which slits serving as fixing means for fixing a leading end portion of a surgical hook, are added to the base body.

The retractor 1 shown in a front view in FIG. 8 includes slits 11, 11, which are long in the longitudinal direction U, in a center portion in the longitudinal direction U of the base body 2.

Figure 9:
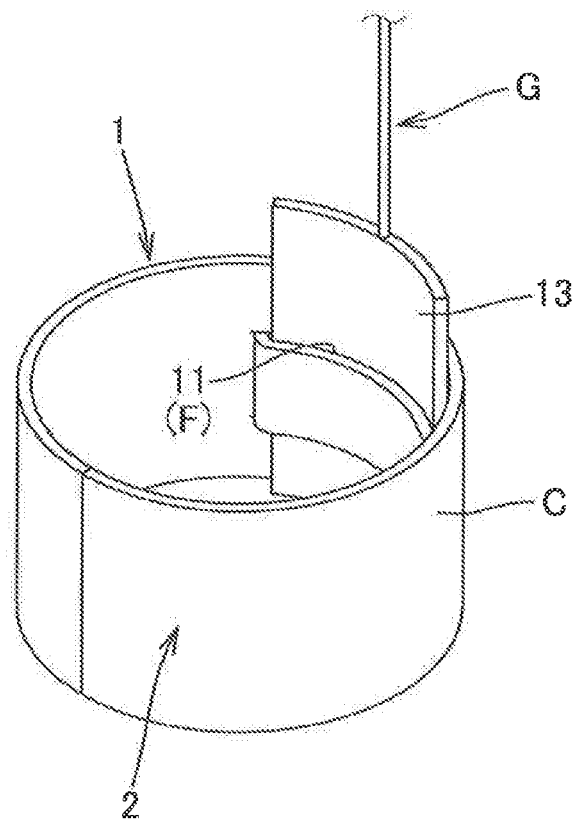
FIG. 9 is a perspective view showing a form in which the base body is deformed into a cylindrical shape, and shows a state in which the leading end portion of the surgical hook is inserted in the slits and fixed to the base body.

As shown in a perspective view in FIG. 9, a leading end portion 13 of a surgical hook G is passed through the slits 11, 11, thereby fixing the leading end portion 13 of the surgical hook G to the base body 2.

Therefore, the slits 11, 11 function as a fixing means F that fixes the leading end portion 13 of the surgical hook G to the base body 2.

In the state shown in FIG. 9, the leading end portion 13 of the surgical hook G may be tied to the base body 2 by means of a thread. In this case, the thread also functions as the fixing means F.

Figure 10:
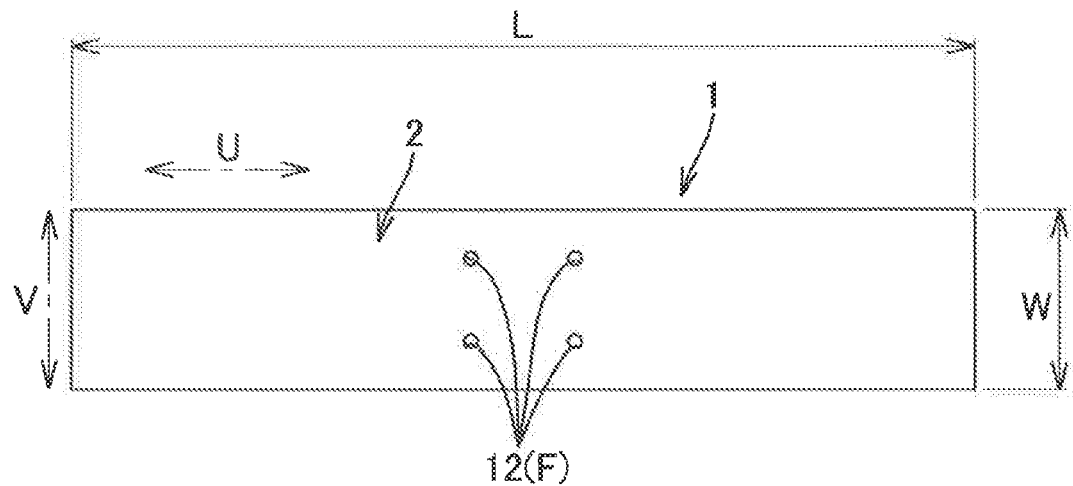
FIG. 10 is a front view of a modification in which through-holes serving as fixing means for fixing the leading end portion of the surgical hook, are added to the base body.

The retractor 1 shown in a front view in FIG. 10 includes through-holes 12, 12, . . . in the thickness direction of the base body 2, in a center portion in the longitudinal direction U of the base body 2.

Figure 11:
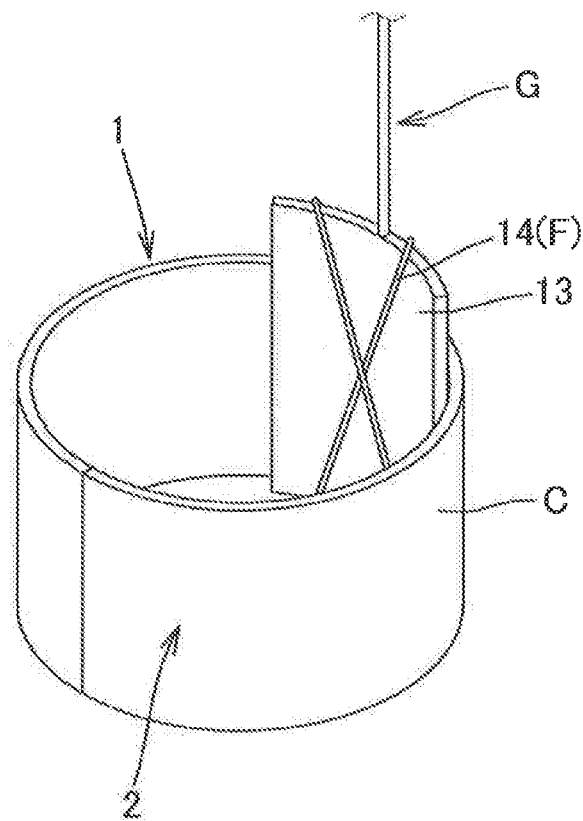
FIG. 11 is a perspective view showing a form in which the base body is deformed into a cylindrical shape, and shows a state that the leading end portion of the surgical hook is fixed to the base body by means of a thread passed through the through-holes.

If a thread 14 is passed through the through-holes 12, 12, . . . shown in FIG. 10 and the leading end portion 13 of the surgical hook G is tied by means of the thread 14 as shown in a perspective view in FIG. 11, the leading end portion 13 of the surgical hook G can be fixed to the base body 2.

Figure 12:
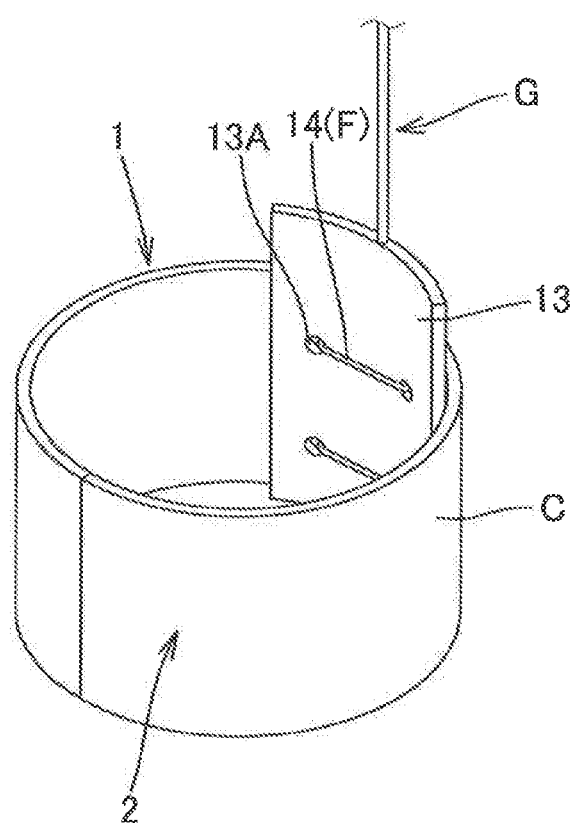
FIG. 12 shows a state that through-holes are also provided in the leading end portion of the surgical hook and the leading end portion of the surgical hook is fixed to the base body by means of a thread passed through the through-holes in the base body and the through-holes in the surgical hook.

Alternatively, if the thread 14 is passed through the through-holes 12, 12, . . . shown in FIG. 10 and the thread 14 is also passed and tied through through-holes 13A, 13A, . . . in the thickness direction provided in the leading end portion 13 of the surgical hook G as shown in a perspective view in FIG. 12, the leading end portion 13 of the surgical hook G can be fixed to the base body 2.

Therefore, the through-holes 12, 12, . . . and the thread 14 function as the fixing means F that fixes the leading end portion 13 of the surgical hook G to the base body 2.

The retractor 1 can easily and assuredly be delivered to the surgical incision made in the body during the surgery, in a state that the leading end portion 13 of the surgical hook G is fixed to the base body 2 by the aforementioned fixing means F to hold the retractor 1 by the surgical hook G. In addition, after the surgery, the retractor 1 can be easily and assuredly taken out of the body through the small incision wound.

Furthermore, the base body 2 of the retractor 1 is fixed to the leading end portion 13 of the surgical hook G, thereby assuredly preventing the retractor 1 from being lost in the body.

DESCRIPTION OF THE REFERENCE CHARACTERS

1 retractor
2 base body
3, 4 bent portion
5, 6 tubular body
5A, 6A through-hole
7, 7A, 7B, 8, 9 protrusion
10A, 10B through-hole
11 slit
12 through-hole
13 leading end portion
13A through-hole
14 thread
A, B surface
C cylindrical face
D, E axis parallel to short direction of rectangle
F fixing means
G surgical hook
L length
T thickness
U longitudinal direction
V short direction
W width

The invention claimed is:

1. A retractor for small-incision endoscopic surgery, the retractor holding a surgical incision made in a body during the surgery in an opened state to ensure a surgical field in the small-incision endoscopic surgery, the retractor comprising
a base body that is a thin plate made of tin having a purity of not less than 99.9%, and has an elongated rectangular shape in an extended state of the base body, wherein the base body does not include a window, and wherein
a width of the base body is selected in a range of 1 to 5 cm and a length of the base body is selected in a range of 3 to 20 cm, in accordance with a size required for a use place, in a state that the base body is extended into a rectangular shape, in order to hold the surgical incision in an opened state; and then a thickness of the base body is selected in a range of 0.5 to 2 mm, in order to ensure flexural rigidity necessary for the use place,
the retractor is inserted from a small incision wound into the body, with the base body being extended into a rectangular shape, or being rounded into a small shape, and
the retractor is delivered to the surgical incision in the body by a surgical instrument used in the small-incision endoscopic surgery, and is used in a state that the base body is bent and deformed into a desired form by the surgical instrument and is applied to the surgical incision.

2. The retractor for small-incision endoscopic surgery according to claim 1, wherein
a bent portion bent in a loop shape about an axis parallel to a short direction of the base body is provided in an end portion in a longitudinal direction of the base body, in a state that the base body is extended into the rectangular shape.

3. The retractor for small-incision endoscopic surgery according to claim I, wherein a tubular body having a through-hole parallel to a short direction of the base body is provided in an end portion in a longitudinal direction of the base body, in a state that the base body is extended into the rectangular shape.

4. The retractor for small-incision endoscopic surgery according to claim 1, wherein
the base body has, on one or both surfaces thereof, an anti-slip protrusion.

5. The retractor for small-incision endoscopic surgery according to claim 1, wherein
the base body is deformed into a cylindrical shape, and has protrusions arranged in a helical manner on a cylindrical face of the cylindrical shape.

6. The retractor for small-incision endoscopic surgery according to claim 1, wherein
a through-hole in a thickness direction of the base body is provided in an end portion in a longitudinal direction of the base body, in a state that the base body is extended into the rectangular shape.

7. A retractor for small-incision endoscopic surgery, the retractor holding a surgical incision made in a body during the surgery in an opened state to ensure a surgical field in the small-incision endoscopic surgery, the retractor comprising:
a base body that is a thin plate made of tin having a purity of not less than 99.9%, and has an elongated rectangular shape in an extended state of the base body, wherein the base body does not include a window;
a width of the base body is selected in a range of 1 to 5 cm and a length of the base body is selected in a range of 3 to 20 cm, in accordance with a size required for a use place, in a state that the base body is extended into a rectangular shape, in order to hold the surgical incision in an opened state; and then a thickness of the base body is selected in a range of 0.5 to 2 mm, in order to ensure flexural rigidity necessary for the use place, and
a fixing means configured to fix a leading end portion of a surgical hook to the base body, wherein
the retractor is inserted from a small incision wound into the body, with the base body being extended into a rectangular shape, or being rounded into a small shape, in a state that the leading end portion of the surgical hook is fixed to the base body by the fixing means to hold the retractor by the surgical hook, and
the retractor is delivered to the surgical incision in the body by the surgical hook, and is used in a state that the base body is bent and deformed into a desired form by a surgical instrument used in the small-incision endoscopic surgery, and is applied to the surgical incision.

8. The retractor for small-incision endoscopic surgery according to claim 7, wherein
a bent portion bent in a loop shape about an axis parallel to a short direction of the base body is provided in an end portion in a longitudinal direction of the base body, in a state that the base body is extended into the rectangular shape.

9. The retractor for small-incision endoscopic surgery according to claim 7, wherein
a tubular body having a through-hole parallel to a short direction of the base body is provided in an end portion in a longitudinal direction of the base body, in a state that the base body is extended into the rectangular shape.

10. The retractor for small-incision endoscopic surgery according to claim 7, wherein
the base body has, on one or both surfaces thereof, an anti-slip protrusion.

11. The retractor for small-incision endoscopic surgery according to claim 7, wherein
the base body is deformed into a cylindrical shape, and has protrusions arranged in a helical manner on a cylindrical face of the cylindrical shape.

* * * * *